United States Patent
Horigome et al.

(10) Patent No.: US 10,585,041 B2
(45) Date of Patent: Mar. 10, 2020

(54) SAMPLE ANALYSIS SYSTEM, DISPLAY METHOD, AND SAMPLE ANALYSIS METHOD

(71) Applicant: Hitachi High-Tech Science Corporation, Minato-ku, Tokyo (JP)

(72) Inventors: Jun Horigome, Tokyo (JP); Masaki Watanabe, Tokyo (JP); Katsutoshi Shimizu, Tokyo (JP); Hideyuki Sakamoto, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 0 days.

(21) Appl. No.: 16/193,021

(22) Filed: Nov. 16, 2018

(65) Prior Publication Data

US 2019/0154579 A1 May 23, 2019

(30) Foreign Application Priority Data

Nov. 17, 2017 (JP) .................................. 2017-221933

(51) Int. Cl.
*G01N 21/64* (2006.01)
*G01N 30/24* (2006.01)
(Continued)

(52) U.S. Cl.
CPC ........... *G01N 21/645* (2013.01); *G01N 30/24* (2013.01); *G01N 30/8675* (2013.01);
(Continued)

(58) Field of Classification Search
CPC .... G01N 30/24; G01N 30/74; G01N 30/8675; G01N 21/645; G01N 2021/6417; H01J 49/0036
See application file for complete search history.

(56) References Cited

U.S. PATENT DOCUMENTS

2012/0223225 A1* 9/2012 Russell .............. G01N 21/6486
250/288
2015/0192590 A1* 7/2015 Sodeoka ................ G01N 21/65
435/6.1

FOREIGN PATENT DOCUMENTS

JP    2009-180706 A    8/2009
JP       5856741 B2    2/2016

OTHER PUBLICATIONS

Li, Wen-Tao, et al. "Characterization of Dissolved Organic Matter in Municipal Wastewater Using Fluorescence PARAFAC Analysis and Chromatography Multi-Excitation/Emission Scan: A Comparative Study." Environmental Science & Technology, vol. 48, No. 5, 2014, pp. 2603-2609.

* cited by examiner

*Primary Examiner* — Nicole M Ippolito
*Assistant Examiner* — Sean M Luck
(74) *Attorney, Agent, or Firm* — Banner & Witcoff, Ltd.

(57) ABSTRACT

A sample analysis system includes a Fluorescence Spectrophotometer, a liquid chromatography device, a mass spectrometer, a control device, and a sample introducer. The Fluorescence Spectrophotometer obtains a three-dimensional fluorescence spectrum including an excitation wavelength, a fluorescence wavelength, and a fluorescence intensity. The liquid chromatography device obtains a three-dimensional absorption spectrum including an elution time, an absorption wavelength, and an absorbance. The mass spectrometer obtains a three-dimensional mass spectrum including an elution time, mass information, and an ion intensity. The axes of respective spectra are set on the same scale, and the mass-charge ratio in the three-dimensional mass spectrum data obtained by the mass spectrometer is determined.

14 Claims, 16 Drawing Sheets

(51) Int. Cl.
*G01N 30/74* (2006.01)
*H01J 49/00* (2006.01)
*G01N 30/86* (2006.01)
*G01N 30/02* (2006.01)

(52) U.S. Cl.
CPC .......... *H01J 49/0036* (2013.01); *G01N 30/74* (2013.01); *G01N 2021/6417* (2013.01); *G01N 2030/027* (2013.01)

SAMPLE ANALYSIS SYSTEM, DISPLAY METHOD, AND SAMPLE ANALYSIS METHOD

This application claims priority from Japanese Patent Application No. 2017-221933 filed on Nov. 17, 2017, the entire subject-matter of which is incorporated herein by reference.

TECHNICAL FIELD

The disclosure relates to a sample analysis system, a display method, and a sample analysis method.

BACKGROUND

A three-dimensional fluorescence spectrum obtained by a Fluorescence Spectrophotometer is effective to recognize an excitation wavelength, a fluorescence wavelength, and a fluorescence intensity of a fluorescence substance contained in a sample. However, when a fluorescence peak appears in the three-dimensional fluorescence spectrum, in a case where the fluorescence substance contained in the sample is unknown, it is not easy to specify what the substance is. Most of them are estimated from the peak information of the excitation wavelength and the fluorescence wavelength by referring to past report examples, but usually a sample contains a plurality of components, and in a case where peaks of the components overlap and a plurality of candidate peaks for the excitation wavelength and the fluorescence wavelength are located adjacent to each other, there may be no past report example, which hinders specification of a substance.

Recognizing the mass information of a component greatly contributes to substance identification. In a case where there is a plurality of candidate components in the past report example, it is possible to narrow down the candidates based on the mass information. In Li, Wen-Tao, et al. "Characterization of dissolved organic matter in municipal wastewater using fluorescence PARAFAC analysis and chromatography multi-excitation/emission scan: a comparative study." Environmental science & technology 48.5 (2014): 2603-2609 (which will be referred to as NPL 1, an abbreviation of Non-Patent Literature 1), a method using a size exclusion column of a high-performance liquid chromatograph and fluorescence wavelength information of a fluorescence detector to obtain mass information has been proposed. Since an elution time changes for each molecular weight in the size exclusion column, it is possible to estimate the molecular weight, based on the elution time of a target sample, by measuring the calibration sample having a plurality of known molecular weights and recognizing the relationship between the molecular weight and the elution time in advance.

A three-dimensional fluorescence spectrum (an elution time, a fluorescence wavelength, and a fluorescence intensity) of each sample component separated by the column is measured by using a fluorescence detector as a detector of a liquid chromatograph, and it is determined whether the measured fluorescence wavelength matches the fluorescence wavelength of the target component of the three-dimensional fluorescence spectrum obtained by the Fluorescence Spectrophotometer, that is, it is a target component, so it is possible to estimate the molecular weight based on the elution time of the component (JP-A-2009-180706). In order to calculate the concentration of a component to be measured (aflatoxin) contained in the sample, the three-dimensional fluorescence spectrum is measured by adding an aflatoxin solution having a different concentration to the sample, so the relationship between the excitation fluorescence wavelength and the concentration is obtained and a calibration model is generated (Japanese Patent No. 5856741).

When a fluorescence peak appears in the three-dimensional fluorescence spectrum, in a case where a fluorescence substance contained in the sample is unknown, it is not easy to specify the substance. There are methods of JP-A-2009-180706 and Japanese Patent No. 5856741 in which molecular weight is estimated from elution time by measuring a calibration sample in a measurement system using a size exclusion column and a fluorescence detector, but in these methods, it is necessary to recognize in advance the relationship between the molecular weight and the elution time in the calibration sample having a plurality of known molecular weights, and since the molecular weight obtained is a predicted value for the calibration sample, the accuracy of molecular weight is not high. Therefore, as described in NPL 1, components are predicted in advance, it is effective when recognizing the characteristics of the molecular weight distribution with components such as proteins and humus substances, but it is not suitable when recognizing the molecular weight with unknown component estimation. When using a size exclusion column, there is a problem that it is complicated because it is necessary to prepare a plurality of calibration samples corresponding to the molecular weights after estimating the molecular weights to some extent and to optimize the elution condition according thereto.

SUMMARY

Illustrative aspects of the disclosure provide a sample analysis system, a display method, and a sample analysis method, capable of estimating mass information as information for identifying unknown fluorescence peak in a three-dimensional fluorescence spectrum obtained by a Fluorescence Spectrophotometer.

According to one illustrative aspect of the disclosure, there may be provided a sample analysis system comprising: a Fluorescence Spectrophotometer configured to measure fluorescence emitted by irradiating a sample to be measured with excitation light and to obtain an excitation spectrum indicating a fluorescence intensity with respect to an excitation wavelength and a fluorescence spectrum indicating a fluorescence intensity with respect to a fluorescence wavelength of fluorescence emitted by irradiating the sample with excitation light of a specific wavelength; a liquid chromatography device configured to separate the sample into substances contained according to an elution time, and to obtain an absorption wavelength of each of the substances; a mass spectrometer configured to obtain mass information of each of substances obtained by separation according to the elution time; a display displaying a measurement result; and a controller configured to control the Fluorescence Spectrophotometer, the liquid chromatography device, the mass spectrometer, and the display and to, based on a peak of a fluorescence intensity with respect to a specific excitation wavelength and a peak of an absorbance with respect to a specific absorption wavelength, the peak of the absorbance corresponding to the peak of the fluorescence intensity, display on the display mass information corresponding to the elution time at which at least the peak of the absorbance is obtained, the fluorescence intensity being obtained by the Fluorescence Spectrophotometer, the absorbance being obtained by the liquid chromatography device, the mass information being obtained by the mass spectrometer.

In the sample analysis system according to the disclosure, the Fluorescence Spectrophotometer is configured to obtain a three-dimensional fluorescence spectrum including an excitation wavelength, a fluorescence wavelength, and a fluorescence intensity.

In the sample analysis system according to the disclosure, the liquid chromatography device is configured to obtain a three-dimensional absorption spectrum including the elution time, the absorption wavelength, and an absorbance.

In the sample analysis system according to the disclosure, the liquid chromatography device comprises: a separation column configured to separate the sample into the substances contained according to the elution time; and a diode array detector configured to measure the absorption wavelength of each of the substances separated by the separation column.

In the sample analysis system according to the disclosure, the substances separated by the separation column are introduced into both the diode array detector and the mass spectrometer.

In the sample analysis system according to the disclosure, the mass spectrometer is configured to obtain a three-dimensional mass spectrum including the elution time, the mass information, and an ion intensity.

In the sample analysis system according to the disclosure, the mass information is a mass-charge ratio.

In the sample analysis system according to the disclosure, the mass spectrometer comprises a single or a plurality of mass detectors.

In the sample analysis system according to the disclosure, the sample analysis system further comprises a sample introducer configured to introduce the sample into the sample analysis system, wherein the sample introducer is configured to introduces the sample into the Fluorescence Spectrophotometer, and wherein the Fluorescence Spectrophotometer is configured to introduce the sample into the liquid chromatography device, after obtaining an excitation spectrum.

In the sample analysis system according to the disclosure, the sample analysis system further comprises a sample introducer configured to introduce the sample into the sample analysis system, wherein the sample introducer is configured to introduce the sample into both the Fluorescence Spectrophotometer and the liquid chromatography device.

In the sample analysis system according to the disclosure, the controller is configured to: detect the peak of the fluorescence intensity with respect to the specific excitation wavelength, the fluorescence intensity being obtained by the spectrophotometer; specify the peak of the absorbance with respect to the specific absorption wavelength corresponding to the peak of the fluorescence intensity, the absorbance being obtained by the liquid chromatography device; and specify the mass information corresponding to the elution time at which the peak of the absorbance is obtained, the mass information being obtained by the mass spectrometer.

In the sample analysis system according to the disclosure, wherein the Fluorescence Spectrophotometer is configured to obtain a three-dimensional fluorescence spectrum including an excitation wavelength, a fluorescence wavelength, and a fluorescence intensity, wherein the liquid chromatography device is configured to obtain a three-dimensional absorption spectrum including the elution time, the absorption wavelength, and an absorbance, wherein the mass spectrometer is configured to obtain a three-dimensional mass spectrum including the elution time, the mass information, and an ion intensity, wherein the controller is configured to: set an axis of the excitation wavelength of the three-dimensional fluorescence spectrum and an axis of the absorption wavelength of the three-dimensional absorption spectrum on the same scale; and set an axis of the elution time of the three-dimensional absorption spectrum and an axis of the elution time of the three-dimensional mass spectrum on the same scale, and wherein the controller is configured to control the display to display the three-dimensional fluorescence spectrum, the three-dimensional absorption spectrum, and the three-dimensional mass spectrum side by side.

According to another illustrative aspect of the disclosure, there may be provided a display method using a sample analysis system, the sample analysis system comprising a Fluorescence Spectrophotometer, a liquid chromatography device, a mass spectrometer, and a display displaying a measurement result, the display method comprising: setting an axis of an excitation wavelength of a three-dimensional fluorescence spectrum obtained by the Fluorescence Spectrophotometer and an axis of an absorption wavelength of a three-dimensional absorption spectrum obtained by the liquid chromatography device on the same scale; setting an axis of an elution time of the three-dimensional absorption spectrum and an axis of an elution time of a three-dimensional mass spectrum on the same scale, the three-dimensional mass spectrum being obtained by the mass spectrometer; and controlling the display to display the three-dimensional fluorescence spectrum, the three-dimensional absorption spectrum, and the three-dimensional mass spectrum side by side.

According to still another illustrative aspect of the disclosure, there may be provided a sample analysis method implemented using a sample analysis system, the sample analysis system comprising a Fluorescence Spectrophotometer, a liquid chromatography device, and a mass spectrometer, the sample analysis method comprising: detecting a peak of a fluorescence intensity for a specific excitation wavelength, the fluorescence intensity being obtained by the spectrophotometer; specifying a peak of an absorbance with respect to a specific absorption wavelength corresponding to the peak of the fluorescence intensity, the absorbance being obtained by the liquid chromatography device; and specifying mass information corresponding to an elution time at which the peak of the absorbance is obtained, the mass information being obtained by the mass spectrometer.

In a sample analysis system, a display method, and a sample analysis method of the disclosure, axes of respective spectra obtained by a Fluorescence Spectrophotometer, a liquid chromatography device, and a mass spectrometer are adjusted, and an unknown substance can be estimated based on mass information (mass-charge ratio: m/z) of a fluorescence component appearing as a peak in a three-dimensional fluorescence spectrum.

BRIEF DESCRIPTION OF THE DRAWINGS

FIGS. 5A and 5B are graphs showing a correlation between a fluorescence intensity of the Fluorescence Spectrophotometer and an absorbance of a liquid chromatography device according to the disclosure, in which FIG. 5A shows an excitation spectrum, and FIG. 5B shows an absorption spectrum;

FIGS. 8A to 8C are graphs displayed on a display unit of the sample analysis system according to the disclosure, in which FIG. 8A shows an excitation spectrum, FIG. 8B shows a fluorescence spectrum, and FIG. 8C shows a three-dimensional fluorescence spectrum;

FIGS. 11A and 11B are flowcharts following FIG. 7, and show procedures for estimating mass information as information for identifying an unknown fluorescence peak, in which FIG. 11A shows a first flow, and FIG. 11B shows a second flow;

DETAILED DESCRIPTION

Hereinafter, preferred illustrative embodiments of a sample analysis system according to the disclosure will be described in detail with reference to FIGS. 1 to 16.

Figure 1:
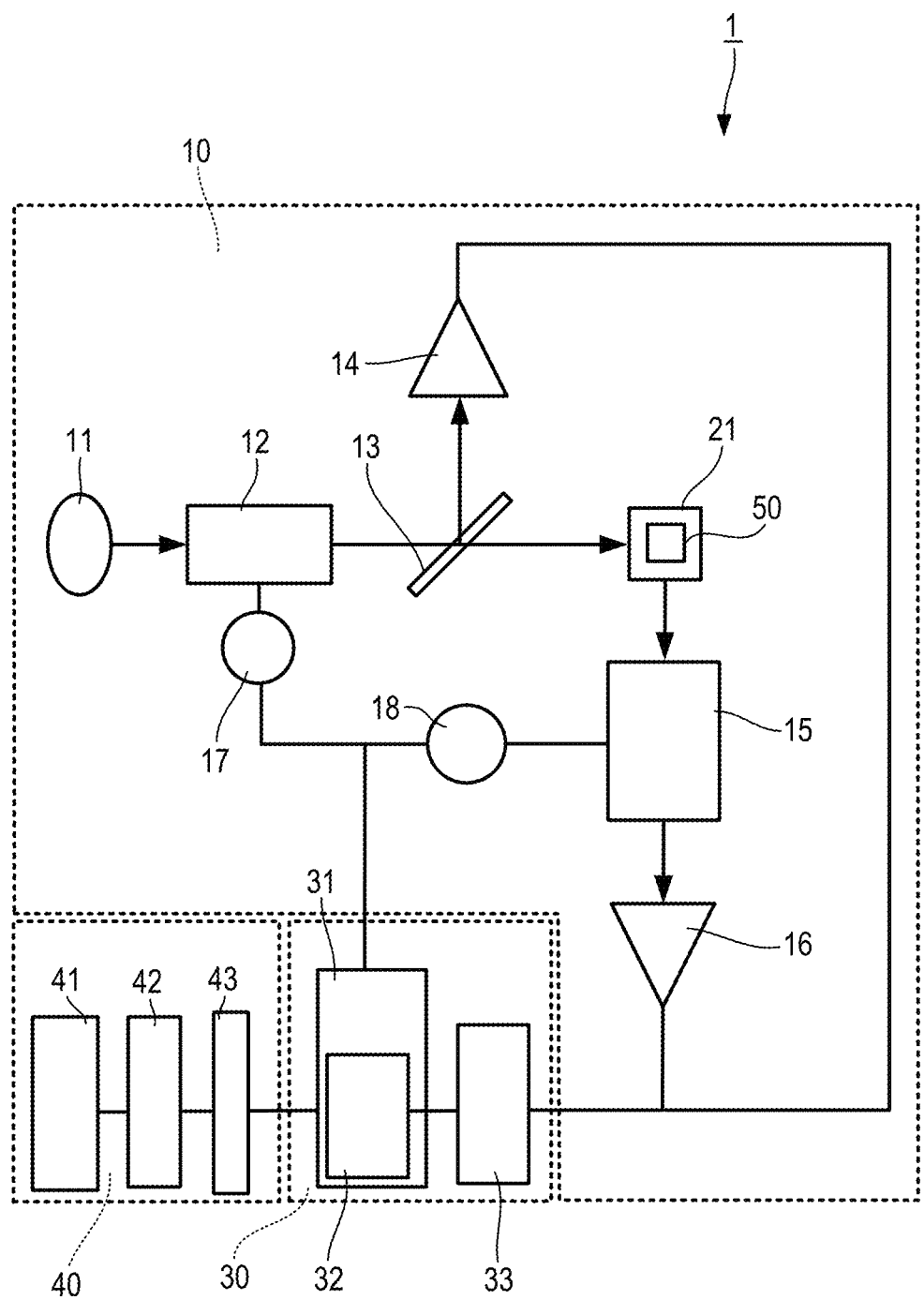
FIG. 1 is a configuration block diagram showing an illustrative embodiment of a Fluorescence Spectrophotometer used in a sample analysis system according to the disclosure.

FIG. 1 is a configuration block diagram showing an illustrative embodiment of a Fluorescence Spectrophotometer used in a sample analysis system according to the disclosure. The configuration of the Fluorescence Spectrophotometer will be described in detail with reference to FIG. 1.

The Fluorescence Spectrophotometer 1 is an apparatus that measures fluorescence emitted from a sample by irradiating the sample with excitation light, and includes a photometer unit 10, a data processing unit 30 that is disposed within the photometer unit 10 and controls the photometer unit 10 to analyze the sample, and an operation unit 40 for inputting and outputting data.

The photometer unit 10 includes a light source 11, an excitation-side spectroscope 12 that spectrally separates light from the light source 11 to generate excitation light, a beam splitter 13 that spectrally separates the light from the excitation-side spectroscope 12, a monitor detector 14 that measures the intensity of a part of the light spectrally separated by the beam splitter 13, a fluorescence-side spectroscope 15 that spectrally separates the fluorescence emitted from the sample into monochromatic light, a detector (fluorescence detector) 16 that detects an electric signal of monochromatic fluorescence, an excitation-side pulse motor 17 that drives the diffraction grating of the excitation-side spectroscope 12, and a fluorescence-side pulse motor 18 that drives the diffraction grating of the fluorescence-side spectroscope 15. The photometer unit 10 further includes a sample setting portion 21 for setting a sample container 50 that contains and holds a sample to be measured. The excitation light from the beam splitter 13 is incident on the sample container 50, and the fluorescence emitted from the sample is incident on the fluorescence-side spectroscope 15. The position of the sample setting portion 21 may be adjustable such that the excitation light from the beam splitter 13 can appropriately be incident on the sample container 50.

The data processing unit 30 includes a computer 31, a central processing portion 32 disposed in the computer 31, and an A/D converter 33 that performs digital conversion of fluorescence from a sample. The operation unit 40 includes an operation panel 41 for an operator to input an input signal necessary for processing of the computer 31, a display device 42 that displays various analysis results processed by the computer 31, and an interface 43 that connects the operation panel 41, the display device 42, and the computer 31.

In accordance with the measurement condition entered by the operator through the operation panel 41, the computer 31 outputs a signal to the excitation-side pulse motor 17 and the excitation-side pulse motor 17 is driven so that the excitation-side spectroscope 12 is set to the target wavelength position. In accordance with the measurement conditions, the computer 31 outputs a signal to the fluorescence-side pulse motor 18, and the fluorescence-side pulse motor 18 is driven so that the fluorescence-side spectroscope 15 is set to the target wavelength position. The excitation-side spectroscope 12 and the fluorescence-side spectroscope 15 have optical elements such as a diffraction grating having a predetermined slit width and a prism, and spectrum scanning becomes possible by using the excitation-side pulse motor 17 and the fluorescence-side pulse motor 18 as power sources, and rotating the optical element through a driving system component such as a cam.

Figure 2:
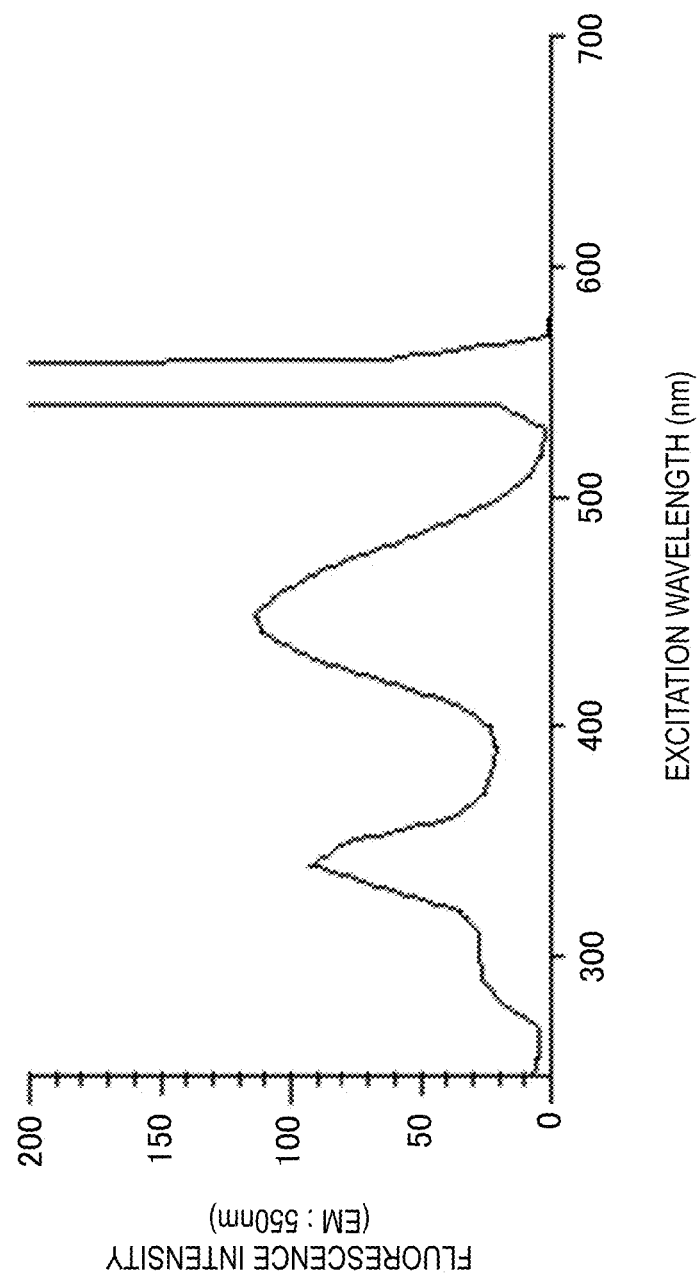
FIG. 2 is a graph showing an excitation spectrum obtained by the Fluorescence Spectrophotometer according to the disclosure.

The excitation spectrum shown in FIG. 2 is a spectrum obtained by measuring the fluorescence intensity when the excitation wavelength of the excitation light is changed with respect to the sample in the sample container 50. The excitation-side spectroscope 12 changes the excitation wavelength from the measurement start wavelength to the measurement end wavelength and irradiates a sample with excitation light of each wavelength. The change in the fluorescence of a specific wavelength is detected by the detector 16 through the fluorescence-side spectroscope 15 set to the fixed wavelength at that time, and is taken into the computer 31 through the A/D converter 33, as a signal intensity. The computer 31 (central processing portion 32) analyzes the signal intensity and displays spectrum on the display device 42.

The display device 42 displays a two-dimensional excitation spectrum of an excitation wavelength and a fluorescence intensity as shown in FIG. 2, as a measurement result. The spectrum (graph) in FIG. 2 shows the fluorescence intensity (arbitrary unit) when the excitation wavelength is changed at a specific fluorescence wavelength (for example, 550 nm).

Figure 3:
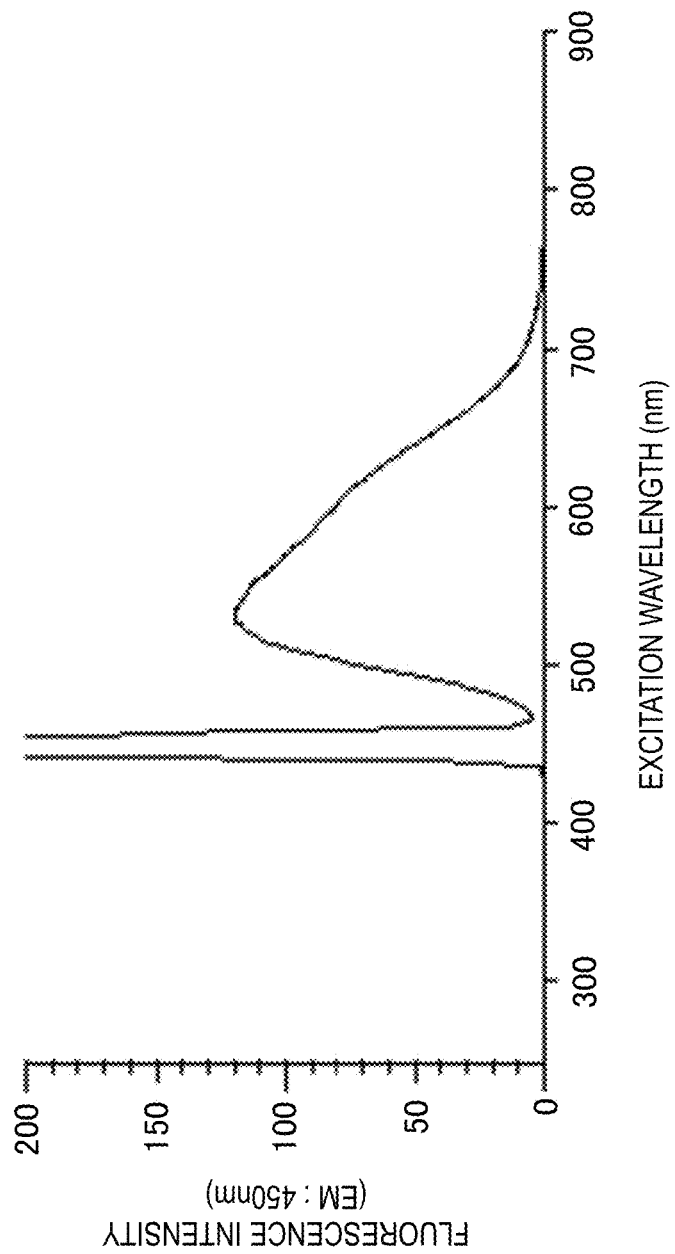
FIG. 3 is a graph showing a fluorescence spectrum obtained by the Fluorescence Spectrophotometer according to the disclosure.

The fluorescence spectrum shown in FIG. 3 is a spectrum obtained by irradiating a sample in the sample container 50 with excitation light of a fixed wavelength and measuring the fluorescence intensity for each wavelength when the fluorescence wavelength is changed. The sample is irradiated with excitation light from the excitation-side spectroscope 12 set to a fixed wavelength. The fluorescence-side spectroscope 15 changes the fluorescence to be measured at that time from the measurement start wavelength to the measurement end wavelength, and the change in the fluorescence for each wavelength is detected by the detector 16, and is taken into the computer 31 through the A/D converter 33, as a signal intensity. The computer 31 (central processing portion 32) analyzes the signal intensity and displays spectrum on the display device 42.

The display device 42 displays a two-dimensional fluorescence spectrum of a fluorescence wavelength and a fluorescence intensity as shown in FIG. 3, as a measurement result. The spectrum of FIG. 3 shows a fluorescence intensity when excitation light has a specific wavelength (for example, 450 nm) and fluorescence wavelength is changed.

Figure 4:
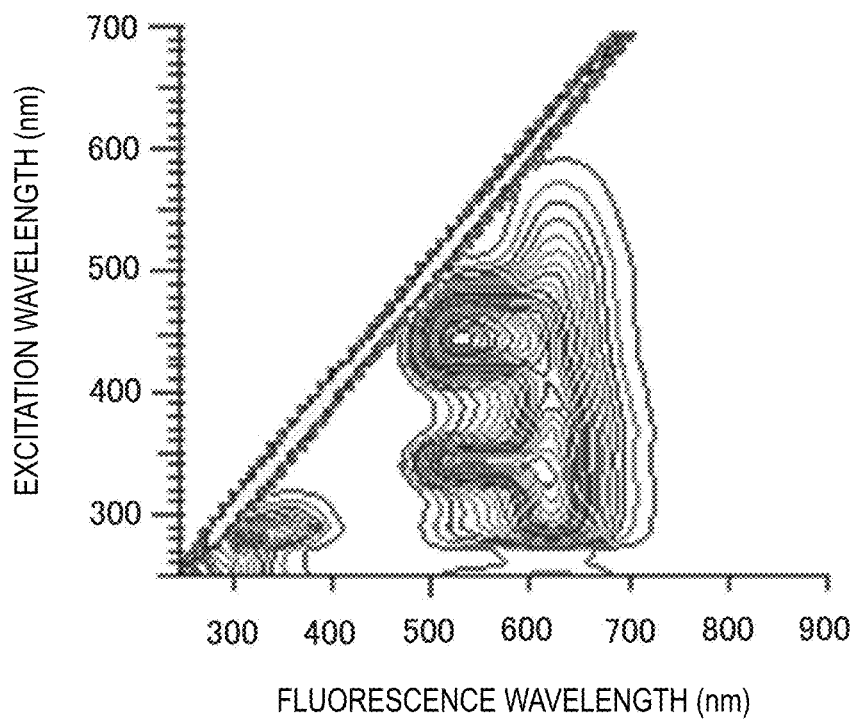
FIG. 4 is a graph showing a three-dimensional fluorescence spectrum obtained based on FIGS. 2 and 3.
Figure 5A:
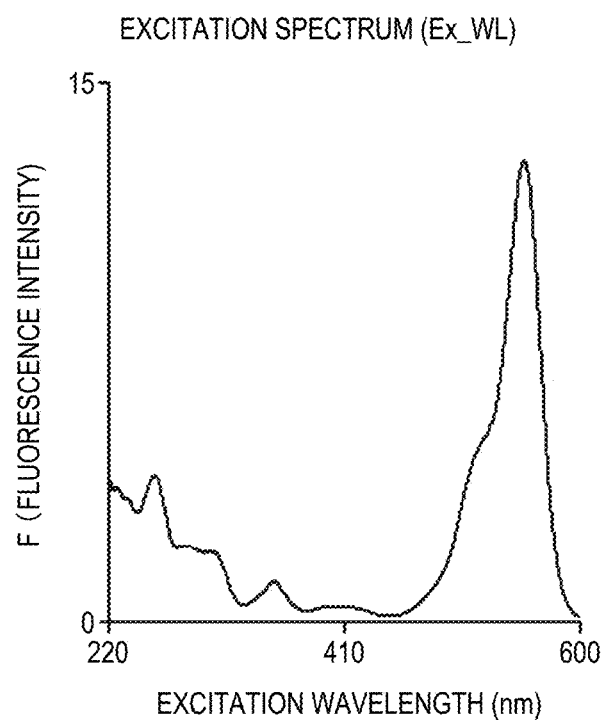
Figure 5B:
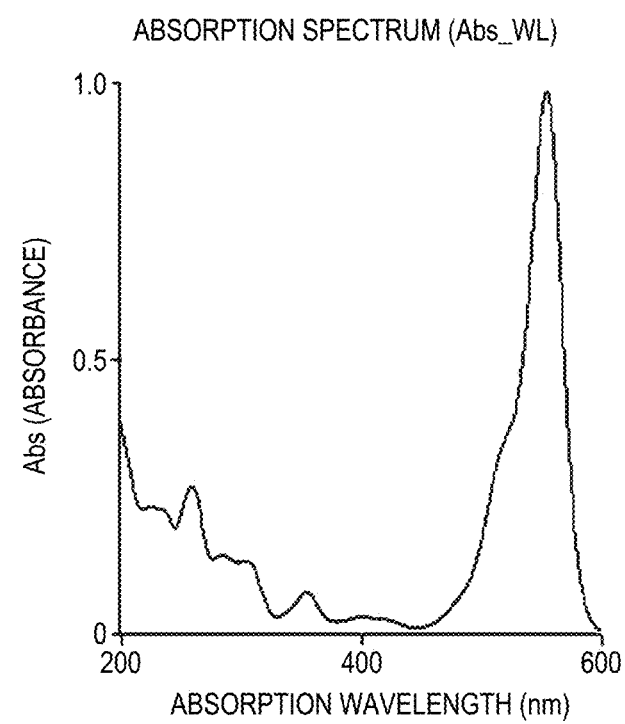

FIG. 4 is a three-dimensional spectrum displayed on the display device 42, and particularly shows a three-dimensional fluorescence spectrum. For the sample, the fluorescence spectrum when the excitation wavelength is fixed is measured, if the fluorescence spectrum scanning is completed, the fluorescence wavelength is returned to the measurement start wavelength, the excitation wavelength is driven by a predetermined wavelength interval, and the fluorescence spectrum at the next excitation wavelength is measured. The fluorescence spectrum is stored three-dimensionally with an excitation wavelength, a fluorescence wavelength, and a fluorescence intensity, it is repeated until the excitation wavelength reaches the final wavelength, so a three-dimensional fluorescence spectrum can be obtained. This spectrum can be said to be a combination of the excitation spectrum of FIG. 2 and the fluorescence spectrum of FIG. 3.

In the obtained three-dimensional fluorescence spectrum, as shown in FIG. 4, the same fluorescence intensity is connected by a line, respectively, and is depicted in a simulated three-dimensional form such as a contour diagram or a bird's-eye view. The excitation wavelength and the fluorescence wavelength, which are mountains on the contour line, are an excitation wavelength suitable for the measurement of a sample and a characteristic fluorescence wavelength, and the operator can easily recognize the excitation wavelength within the measurement range of a sample and the fluorescence characteristics of the fluorescence wavelength. Such a three-dimensional fluorescence spectrum is useful in that it is possible to obtain a lot of pieces of information such as the number of components of fluorescence substance in a sample and identification of components from that.

The Fluorescence Spectrophotometer 1 can acquire the excitation wavelength, the fluorescence wavelength, and the fluorescence intensity of a sample in a short measurement time, and can specify a substance promptly if it can analyze the peak of the fluorescence intensity and compare it with known information. However, in a case where an unknown substance is detected as the peak of the fluorescence intensity and it is not present in the known information, it is difficult to specify the substance.

Therefore, the inventors have found that 1) there is a correlation between the fluorescence intensity of the Fluorescence Spectrophotometer 1 and the absorbance of the liquid chromatography device 60 to be described later, and 2) the liquid chromatography device 60 separates the substance for each elution time to obtain absorption intensity, and the mass spectrometer 70 to be described later can measure mass information of each of the substance obtained by separation at each elution time. As a result, the inventors have found a sample analysis system 100 which associates a fluorescence intensity with a mass information and smoothly specifies unknown substances, and a method thereof.

With respect to the above-described 1) a correlation between the fluorescence intensity of the Fluorescence Spectrophotometer 1 and the absorbance of the liquid chromatography device 60 to be described later, it is necessary to discuss Lambert-Beer's law. According to the Lambert-Beer's law, the relationship between the fluorescence intensity F and the absorbance Abs ($=\varepsilon cd$) is known to be (Equation) $F=Io(2.303\ \varepsilon cd)\phi_f$.

here,

F: fluorescence intensity

Io: incident light intensity $\varepsilon$: molar extinction coefficient c: concentration d: length of liquid tank (optical path length)

$\phi_f$: quantum yield

As shown in the above equation, A) fluorescence intensity F is represented by $Io(2.303\ \varepsilon cd)\phi_f$. At this time, absorbance Abs becomes $\varepsilon cd$. B) Quantum yield $\phi_f$ is the light emission efficiency of substance, has a substantially constant value regardless of wavelength. Furthermore, C) the incident light intensity (excitation light intensity) Io also has a substantially constant value regardless of wavelength by applying the device function thereto.

From the above, it is understood that the fluorescence intensity F and the absorbance Abs ($\varepsilon cd$) are in a proportional relationship. In addition, it is understood from the above B) and C) that this proportional relationship is also established when the excitation wavelength is changed, and it is understood that the fluorescence intensity for the excitation wavelength and the absorbance for the absorption wavelength are in a proportional relationship. From the graphs shown in FIGS. 5A and 5B obtained by the experiment, the excitation spectrum (FIG. 5A) showing the fluorescence intensity obtained by irradiating a sample (rhodamine B) with light and the absorption spectrum (FIG. 5B) showing the absorption intensity obtained by irradiating the sample with light can be determined to be highly correlated data. That is, there is a correlation between the fluorescence intensity for the excitation wavelength (of the Fluorescence Spectrophotometer 1) and the absorbance (absorption intensity) for the absorption wavelength (of the liquid chromatography device 60), and it is understood that the intensities (the fluorescence intensity and the absorbance) of the excitation spectrum and the absorption spectrum show substantially the same behavior.

Therefore, in a case when a substance having an unknown fluorescence intensity peak at a specific excitation wavelength is detected from the sample by the Fluorescence Spectrophotometer 1, if the sample is measured by the liquid chromatography device 60, the peak of absorbance at substantially the same absorption wavelength is likely to be obtained. Then, as described in above 2), since the mass spectrometer 70 obtains the mass information at the elution time associated with the elution time of the liquid chromatography device 60, the mass information obtained by the mass spectrometer 70 at the same elution time corresponds to the elution time of the liquid chromatography device 60 in which the peak appears, and consequently it can be determined that the mass information of the substance having an unknown fluorescence intensity peak is specified. This leads to the conclusion that substances can be specified more quickly.

Figure 6:
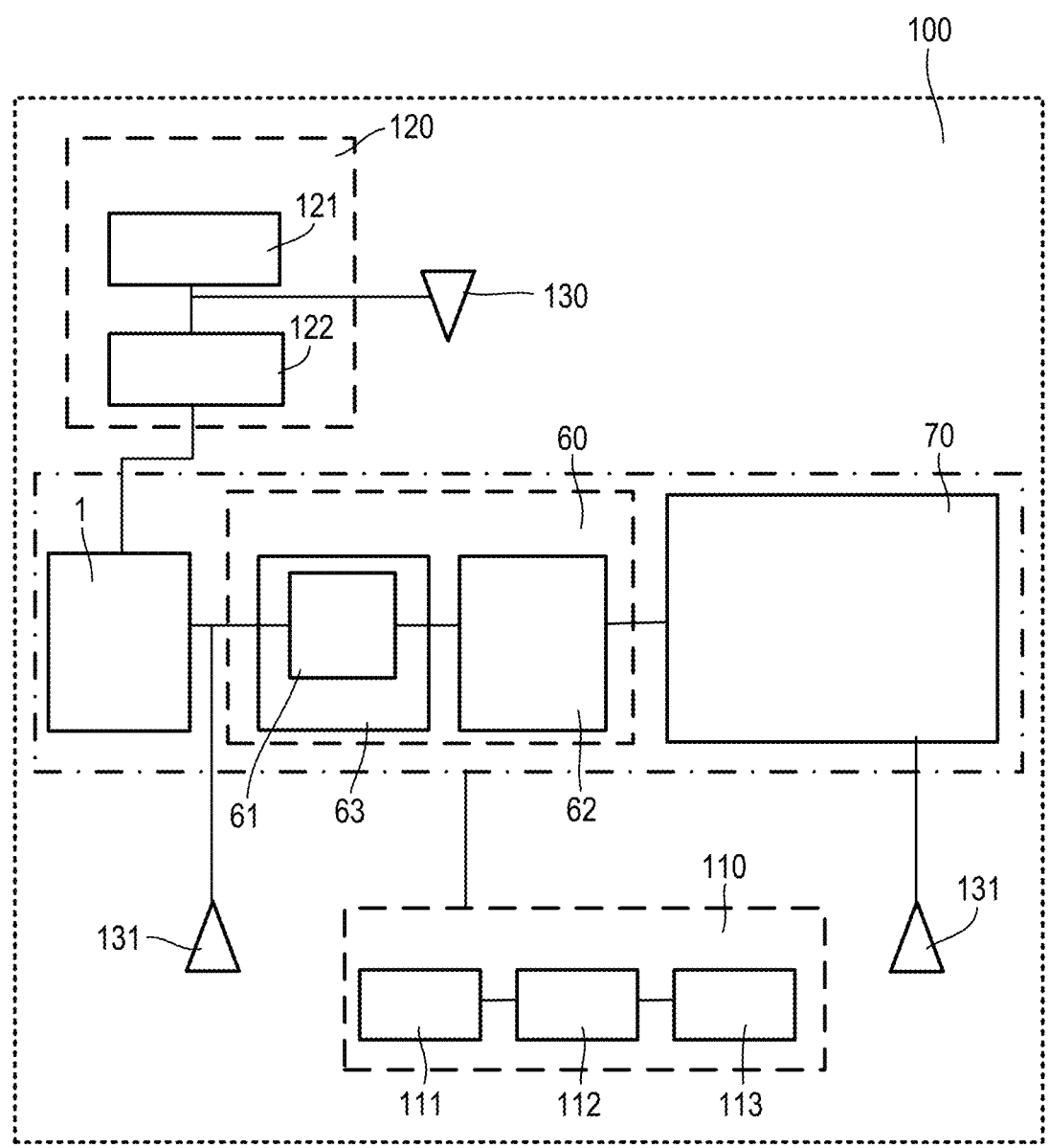
FIG. 6 is a block diagram showing an example of a first embodiment of a sample analysis system according to the disclosure.

FIG. 6 is a block diagram of a sample analysis system according to the disclosure. A first illustrative embodiment of the sample analysis system will be described with reference to FIG. 6.

A sample analysis system 100 includes a Fluorescence Spectrophotometer 1, a liquid chromatography device 60, a mass spectrometer 70, a control device 110, and a sample introduction unit 120.

The Fluorescence Spectrophotometer 1 is an apparatus that obtains a three-dimensional fluorescence spectrum including an excitation wavelength, a fluorescence wavelength, and a fluorescence intensity, and the configuration is detailed in FIG. 1. The liquid chromatography device 60 is a device that separates the sample analyzed by the Fluorescence Spectrophotometer 1 into substances which are contained, according to the elution time, and obtains an absorption wavelength of each of the substances. It includes a separation column 61 and a diode array detector 62, and obtains a three-dimensional absorption spectrum including an elution time, an absorption wavelength, and an absorbance. That is, the separation column 61 separates the sample into substances which are contained, according to the elution time, and the diode array detector 62 measures the absorption wavelength of each of the substances obtained by separation by the separation column 61. Further, the separation column 61 is disposed in column oven 63.

The mass spectrometer 70 is a device that obtains the mass information of each of the substances obtained by separation according to the elution time by the liquid chromatography device 60, and includes, for example, a first mass detection unit that obtains mass information of molecules constituting a substance, for example, molecular weight information, and a second mass detection unit with an $MS^n$ function capable of obtaining mass information of product ions obtained by decomposing molecules, and obtains a three-dimensional mass spectrum including an elution time, mass information, and an ion intensity. The mass information is a mass-charge ratio (m/z) which is the ratio of mass of charged particles and charge. Here, m is the molecular mass, and z is the number of charges. However, the configuration of the mass spectrometer 70 is not particularly limited, and it may be configured with a single mass detection unit, or may have two or more stages and include a plurality of mass detection units with different types of mass information to be detected.

The control device 110 includes a controller 111, a display unit 112, and an input unit 113, and the controller 111 controls the Fluorescence Spectrophotometer 1, the liquid chromatography device 60, and the mass spectrometer 70. The display unit 112 displays measurement conditions, a measurement result, and the like. The input unit 113 is a device to which an operator inputs data necessary for various analyzes and commands to operate various devices and the like. In addition, the data processing unit 30 and the operation unit 40 of the Fluorescence Spectrophotometer 1 may be integrated with the control device 110, or may be independent and linked by a network to share various data.

The controller 111 displays on the display unit 112, mass information obtained by the mass spectrometer 70, corresponding to the elution time at which the peak of the absorbance is obtained, based on a peak of fluorescence intensity with respect to the specific excitation wavelength obtained by the Fluorescence Spectrophotometer 1, and a peak of an absorbance, corresponding to the peak of the fluorescence intensity, with respect to a specific absorption wavelength obtained by the liquid chromatography device 60.

The sample introduction unit 120 introduces a sample into the sample analysis system 100 and includes a liquid delivery portion 121 and a sample introduction portion 122. The sample analysis system 100 includes an eluent portion 130 for storing the eluent to be introduced into the sample introduction portion 122 and a waste liquid portion 131 for storing the discharged eluent. At least one waste liquid portion 131 is disposed. The sample introduction portion 122 is configured with a manual injector for introducing sample with a microsyringe or the like, or an autosampler for introducing a sample placed in a vial with an automatic pipetter.

An example of the procedure of the sample analysis method performed using the sample analysis system 100 will be described with reference to the flowchart of FIG. 7.

The liquid delivery portion 121 of the sample introduction unit 120 delivers the eluent in the eluent portion 130 to the sample introduction portion 122 by a pump or the like. The introduced sample flows along the flow path together with the eluent and is led to the Fluorescence Spectrophotometer 1. Normally, the Fluorescence Spectrophotometer 1 puts a solution sample in a 10 mm square cell and installs it on the sample setting portion 21 for measurement, but in order to use the sample feeding method, and it is desirable to use a flow cell in which a solution of a sample flows forward and backward with respect to the sample setting portion 21, as the sample container 50 of the Fluorescence Spectrophotometer 1 of the disclosure.

Figure 8A:
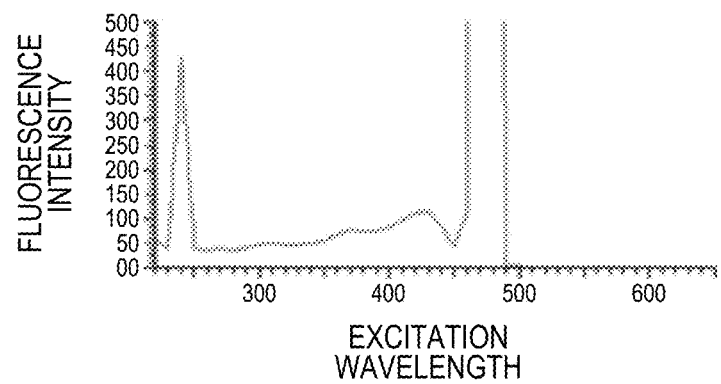
Figure 8B:
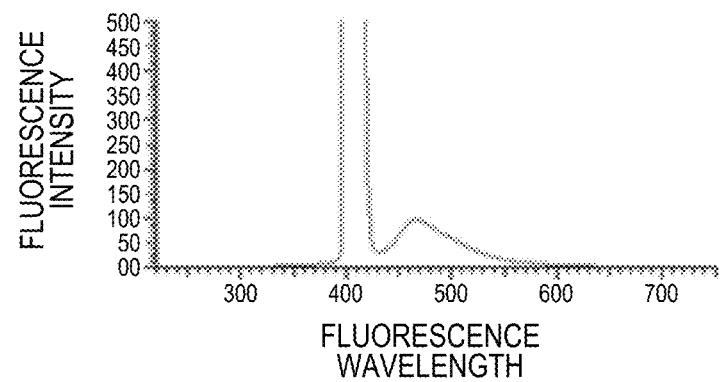
Figure 8C:
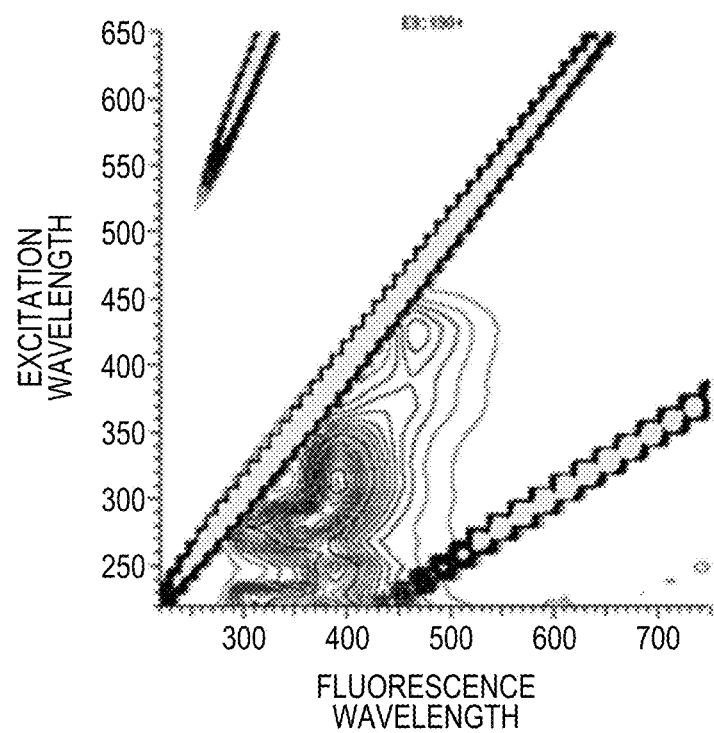

After the sample is introduced into the sample container (flow cell) 50, the Fluorescence Spectrophotometer 1 obtains a three-dimensional fluorescence spectrum (an excitation wavelength, a fluorescence wavelength, and a fluorescence intensity) in all fluorescence components contained in the sample (S10). The three-dimensional fluorescence spectrum is shown in the graph of FIG. 8C. The three-dimensional fluorescence spectrum is a combination of the excitation spectrum of FIG. 8A and the fluorescence spectrum of FIG. 8B.

Since noise occurs by the influence of pulsating flow at the time of measurement, it is desirable that liquid delivery is temporarily stopped or is performed in a state where the flow rate is reduced to a level not affected by the pulsating flow. The sample solution used for the measurement may be irradiated with excitation light and photolyzed. In particular, since the light source 11 of the Fluorescence Spectrophotometer 1 has a large amount of light, it is necessary to pay attention to the photolysis of the components contained in the sample. Therefore, the flow path of the outlet of the flow cell 50 may be branched into two paths, and the sample solution portion used for measurement may be led to the waste liquid portion 131 and discarded. In a case where there is concern about photodegradation, it is desirable to insert a shutter that blocks excitation light in the part of the flow cell 50 of the Fluorescence Spectrophotometer 1 when the sample is delivered as liquid to the next step. In the case of a sample having no influence of photolysis, it may be directly used for the next process.

Subsequently, the sample passing through the flow cell 50 of the Fluorescence Spectrophotometer 1 reaches the separation column 61 of the liquid chromatography device 60. Times for respective components to pass through the separation column 61 are different due to the interaction between the separation column 61 and each component of the sample, so the components are separated according to elution time (S20). Since the elution time depends on the temperature, it is desirable to keep it at a constant temperature in the constant temperature layer 53.

Figure 9:
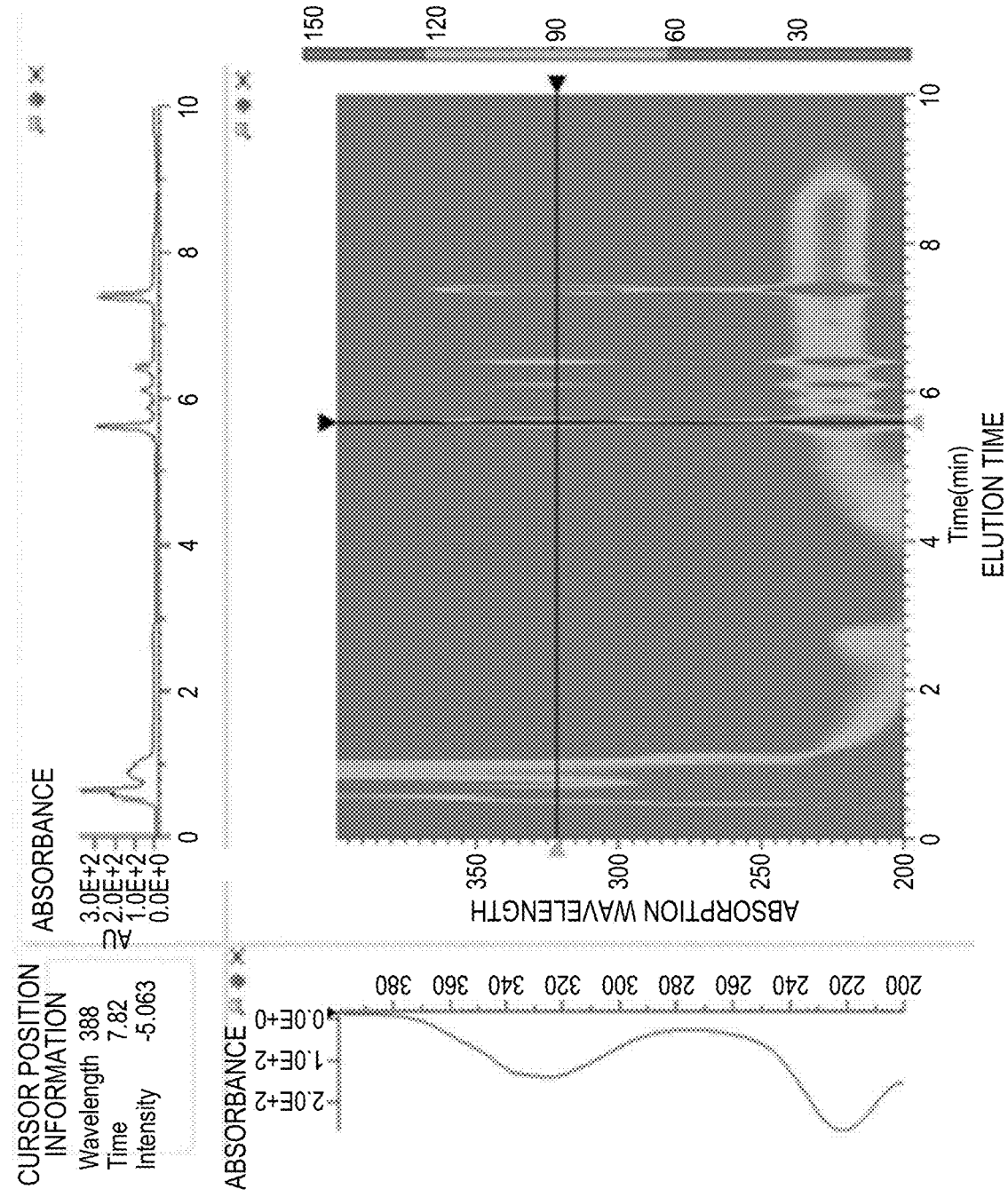
FIG. 9 is a graph showing a three-dimensional absorption spectrum obtained by the liquid chromatography device according to the disclosure.

Each component of the sample that has passed through the separation column 61 is led to a diode array (DAD) detector 62 at a different elution time. Since the diode array detector 62 can measure the absorption spectrum at high speed, here, a three-dimensional absorption spectrum (an elution time, an absorption wavelength, and an absorbance) is obtained (S30). The three-dimensional absorption spectrum is shown in FIG. 9. In the diode array detector 62, the incident light irradiated on the sample has less light amount than the excitation light of the Fluorescence Spectrophotometer 1, so that there is often no influence of photolysis of the components contained in the sample.

Figure 10:
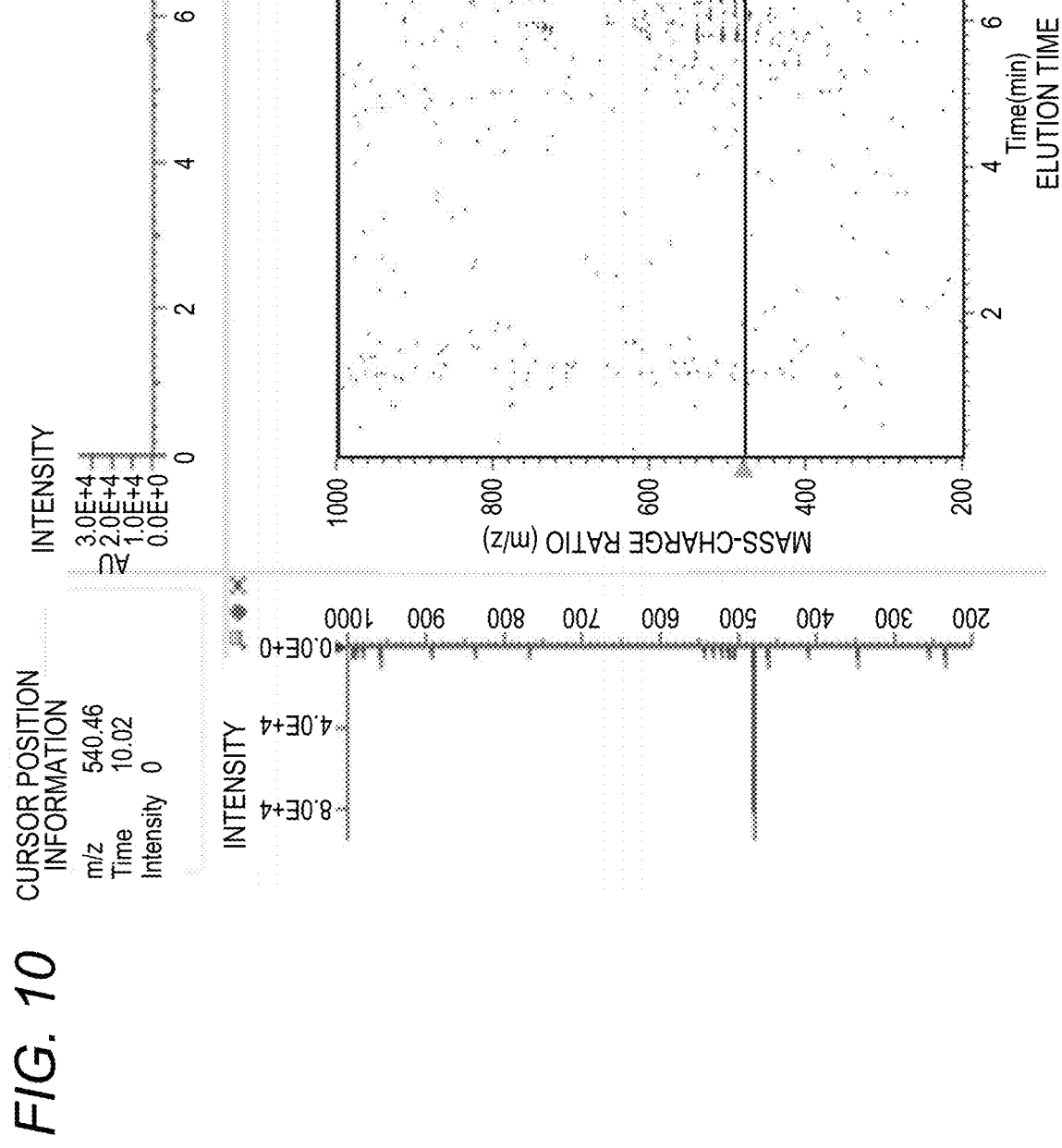
FIG. 10 is a graph showing a three-dimensional mass spectrum obtained by a mass spectrometer according to the disclosure.

Each component of the sample that has passed through the diode array detector 62 is led to the mass spectrometer 70 while maintaining different elution time, and the mass spectrometer 70 obtains a three-dimensional mass spectrum (an elution time, a mass-charge ratio (m/z), and an ion intensity) (S40). The three-dimensional mass spectrum is shown in FIG. 10.

In a case where the mass spectrometer 70 includes, for example, the first mass detection unit and the second mass detection unit described above, the first mass detection unit gases the substance under high vacuum and obtains mass information of the ionized substance (molecule). Then, the second mass detection unit obtains the mass information of the product ion obtained by decomposing the molecule measured by the first mass detection unit. That is, it is possible to obtain molecular weight information with the first mass detection unit and obtain the mass information of the product ion for further estimating the compound with the second mass detection unit.

In the flow described above, since it is performed in conjunction with the elution time in the liquid chromatography device 60, the sample (substance) measured along the solution time is the same.

Figure 11A:
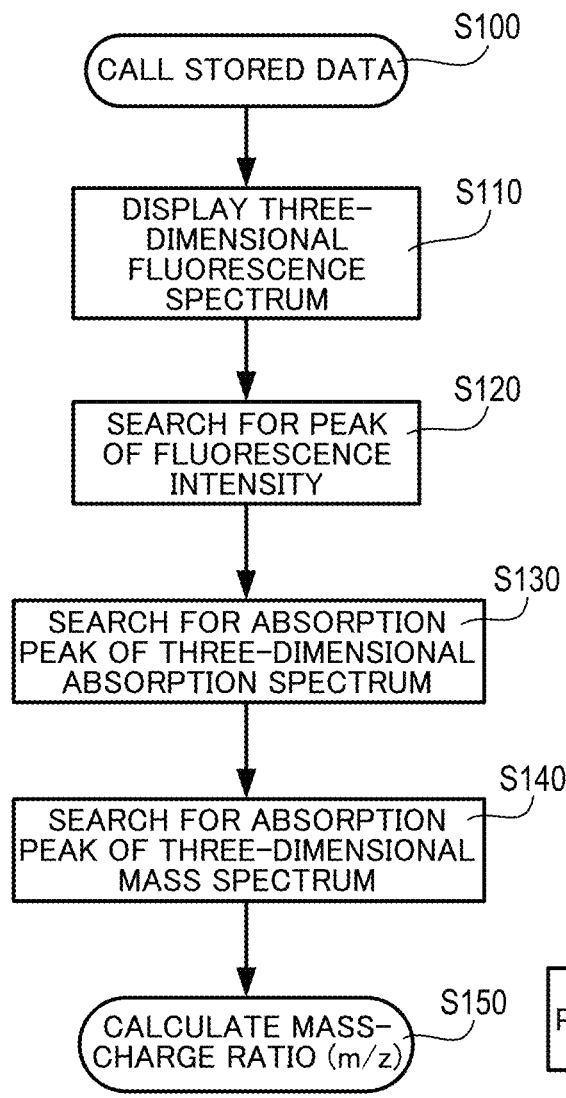
Figure 11B:
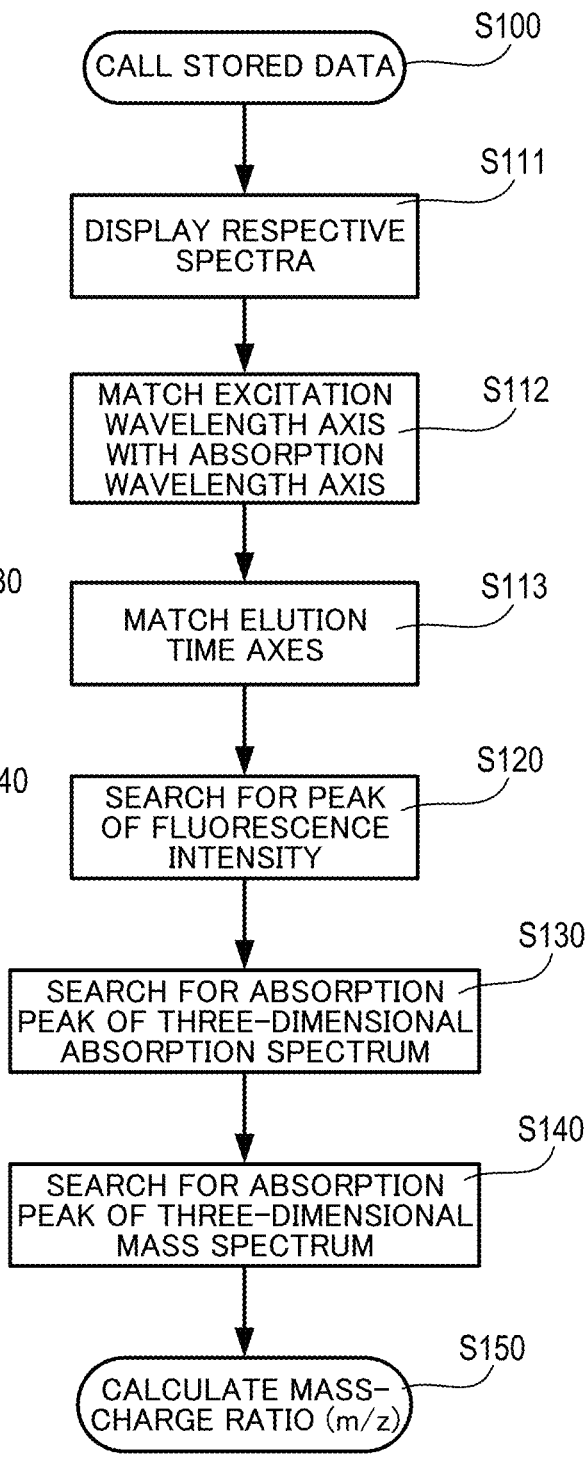

Next, a procedure for estimating mass information (mass-charge ratio: m/z) as information for identifying an unknown fluorescence peak in the three-dimensional fluorescence spectrum obtained by Fluorescence Spectrophotometer 1 will be described based on the flowchart of FIG. 11. FIG. 11A shows the first flow, and FIG. 11B shows the second flow.

Figure 7:
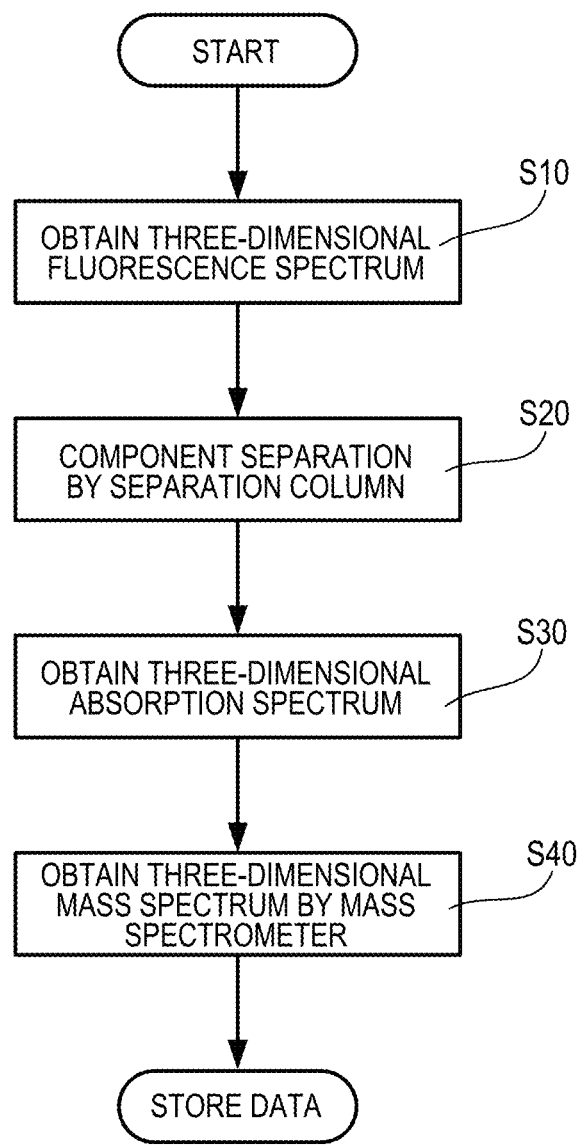
FIG. 7 is a flowchart showing a measurement procedure of the sample analysis system according to the disclosure.

In the first flow, the data stored in the flow of FIG. 7 is called (S100) and only the three-dimensional fluorescence spectrum is displayed on the display unit 112 (see S110 in FIG. 8C). Next, by inputting an operator's processing command, for example, the controller 111 quickly searches for the peak of the fluorescence intensity (S120), searches for an absorption peak in the three-dimensional absorption spectrum data of the liquid chromatography device 60 corresponding thereto (S130), and obtains the elution time of the corresponding absorption peak.

The controller 111 searches for an absorption peak from the three-dimensional absorption spectrum data of the liquid chromatography device 60 and the three-dimensional mass spectrum data of the mass spectrometer 70 with elution time axis coincident (S140), and obtains an elution time of the corresponding absorption peak. The controller 111 calculates the mass-charge ratio (m/z) in the three-dimensional mass spectrum data of the corresponding mass spectrometer 70 from the elution time of the absorption peak (S150).

Figure 12:
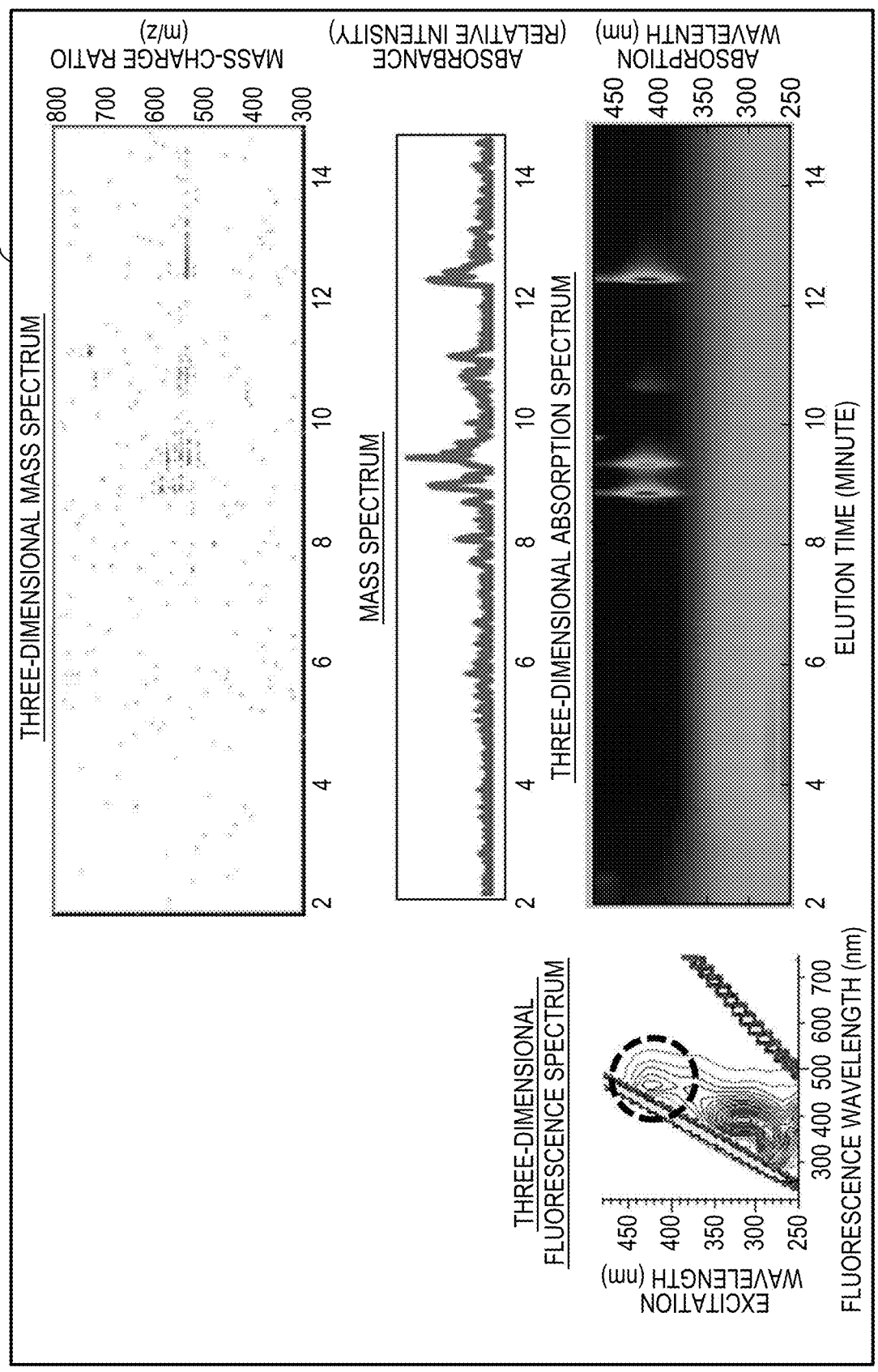
FIG. 12 shows a three-dimensional fluorescence spectrum, a three-dimensional absorption spectrum, and a three-dimensional mass spectrum, which are displayed on the display unit of the sample analysis system according to the disclosure.

In the second flow, the data stored in the flow of FIG. 7 is called (S100), and a three-dimensional fluorescence spectrum, a three-dimensional absorption spectrum related to the three-dimensional fluorescence spectrum, a three-dimensional mass spectrum, or the like are displayed on the display unit 112 in the arrangement of FIG. 12 (S111). The operator matches the scale range of the excitation wavelength axis (Y axis) of the three-dimensional fluorescence spectrum data obtained by the Fluorescence Spectrophotometer 1 with that of the absorption wavelength axis (Y axis) of the three-dimensional absorption spectrum data obtained by the diode array detector 62 of the liquid chromatography device 60 (S112). Subsequently, the elution time axis (X axis) of the three-dimensional absorption spectrum data obtained by the diode array detector 62 is matched with the elution time axis (X axis) of the three-dimensional mass spectrum data of the mass spectrometer 70 (S113).

Thereafter, the operator designates the peak wavelength of the excitation wavelength of the component of interest in the three-dimensional fluorescence spectrum (excitation emission matrix: EEM) data (S120), and searches for an absorption peak of the three-dimensional absorption spectrum data by the liquid chromatography device 60 that matches the absorption peak (S130) to obtain the elution time of the corresponding absorption peak. Thereafter, an absorption peak is searched from the three-dimensional absorption spectrum data of the liquid chromatography device 60 and the three-dimensional mass spectrum data of the mass spectrometer 70 of which elution time axes are matched with each other (S140), and an elution time of the corresponding absorption peak is obtained.

In the sample analysis system 100 of the disclosure, the Fluorescence Spectrophotometer 1 obtains a three-dimensional fluorescence spectrum including an excitation wavelength, a fluorescence wavelength, and a fluorescence intensity, the liquid chromatography device 60 obtains a three-dimensional absorption spectrum including an elution time, an absorption wavelength, and an absorbance, and the mass spectrometer 70 obtains a three-dimensional mass spectrum including an elution time, mass information, and an ion intensity.

Figure 13:
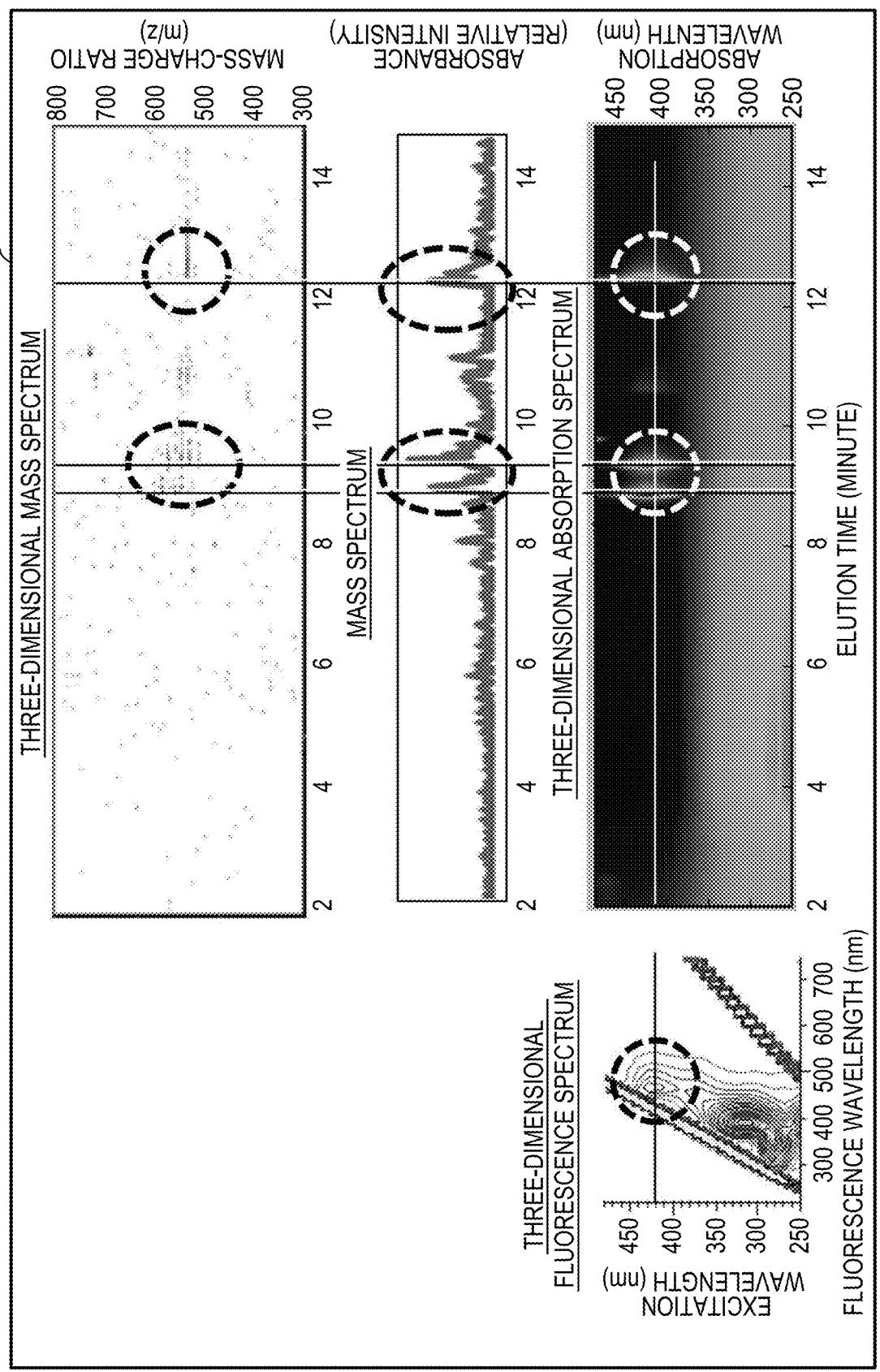
FIG. 13 shows various spectra obtained by performing axis adjustment, axis display, and peak identification on the same display as in FIG. 12.

The controller 111 sets the axis of the excitation wavelength of the three-dimensional fluorescence spectrum and the axis of the absorption wavelength of the three-dimensional absorption spectrum on the same scale, and sets the axis of the elution time of the three-dimensional absorption spectrum and the axis of the elution time of the three-dimensional mass spectrum on the same scale, and the display unit 112 displays the three-dimensional fluorescence spectrum, the three-dimensional absorption spectrum, and the three-dimensional mass spectrum side by side. FIG. 13 is a display obtained by performing axis adjustment, axis display (straight solid line), and peak identification (broken line) on the graph of FIG. 12. In FIG. 12 and FIG. 13, a mass spectrum showing the change in absorbance over an elution time is also displayed. In the process according to the first flow, the display unit 112 may also perform the display of FIGS. 12 and 13.

The method of obtaining the axes of respective spectra may be performed by the operator or by the controller 111 automatically by software, and is not particularly limited. In addition, when the axis is obtained, the specific wavelength range and the like may be narrowed down.

The mass-charge ratio (m/z) in the three-dimensional mass spectrum data of the corresponding mass spectrometer 70 can be determined from the elution time of the absorption peak (S150). As a result, the operator or the like can use the mass information such as the mass-charge ratio, so even if an unknown substance is detected, for example, in the three-dimensional fluorescence spectrum or the like, the type of the substance can be more easily specified. In particular, according to the display method for displaying the screen of the display unit 112 shown in FIGS. 12 and 13 by using the sample analysis system 100, the operator can easily identify peaks through the axis of the scaled absorption wavelength and the axis of the scaled elution time, and can easily obtain mass information of unknown substances.

Figure 14:
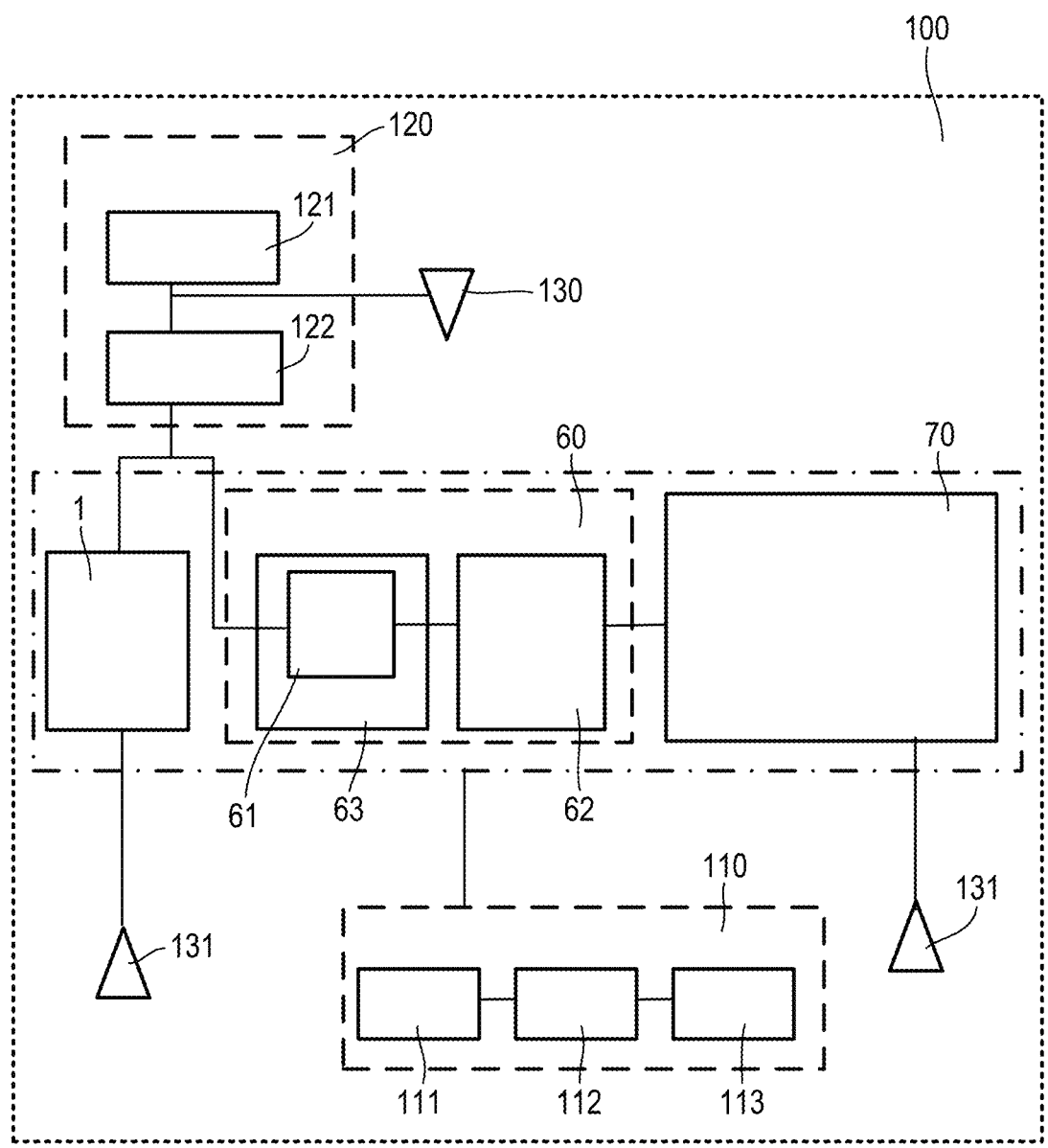
FIG. 14 is a block diagram showing an example of a second embodiment of the sample analysis system according to the disclosure.

FIG. 14 is a block diagram showing a second illustrative embodiment of the sample analysis system 100. A second illustrative embodiment of the sample analysis system 100 will be described with reference to FIG. 14.

In the second illustrative embodiment, the flow path from the sample introduction portion 122 of the sample introduction unit 120 is branched into two flow paths and the flow paths are switched so as to lead one to the Fluorescence Spectrophotometer 1 and the other to the separation column 61 of the liquid chromatography device 60. The sample solution used for the measurement by the Fluorescence Spectrophotometer1 may be photolyzed by excitation light irradiation. In particular, since the light source of the Fluorescence Spectrophotometer 1 has a large amount of light, and it is necessary to pay attention to the photolysis of the components contained in the sample, it is configured such that the sample solution used in the Fluorescence Spectrophotometer 1 is led to the waste liquid portion 131 and discarded and it is possible to introduce a sample in a new state to the flow path after the separation column 61.

Figure 15:
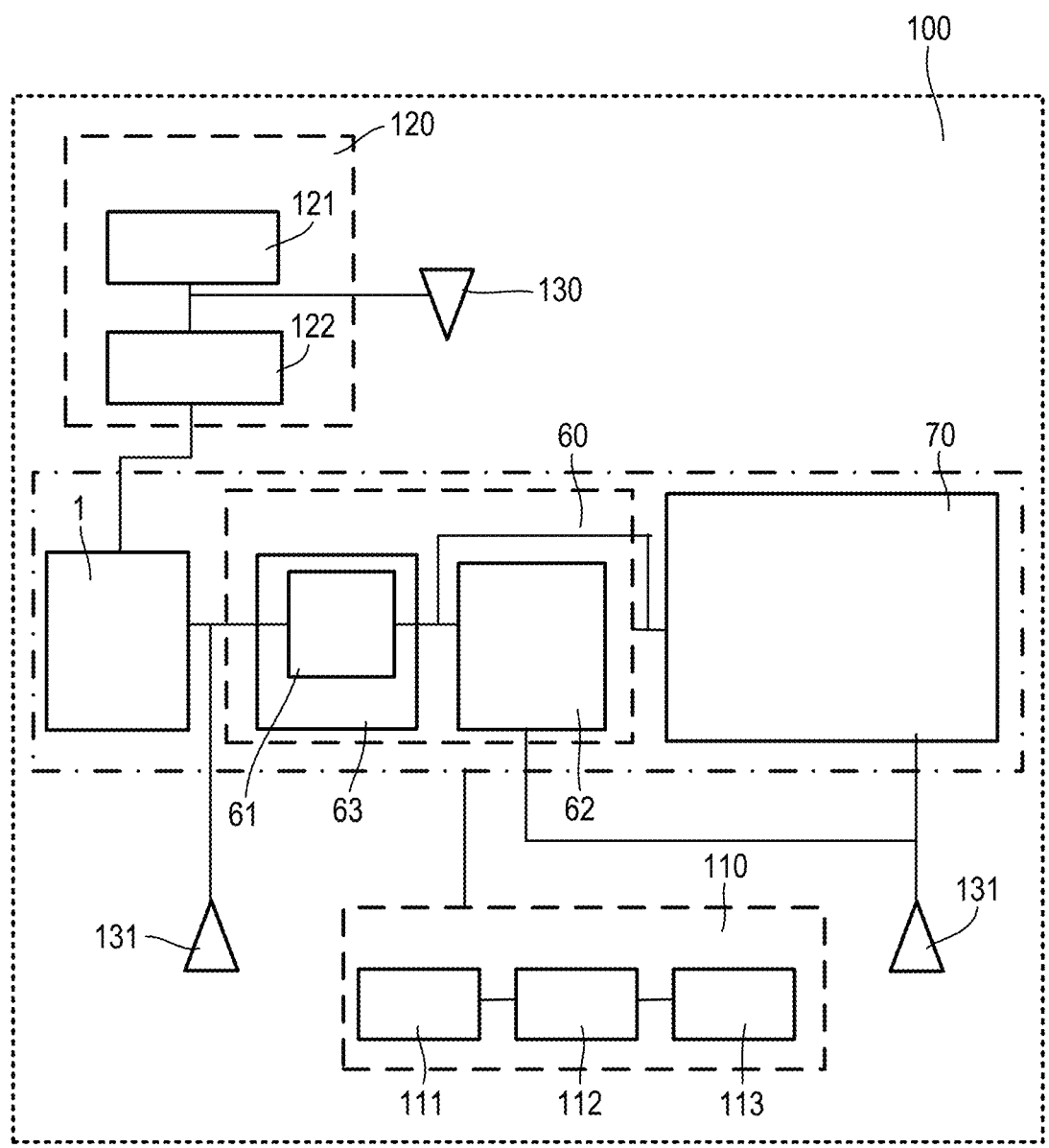
FIG. 15 is a block diagram showing an example of a third embodiment of the sample analysis system according to the disclosure.

FIG. 15 is a block diagram showing a third illustrative embodiment of the sample analysis system 100. The third illustrative embodiment of the sample analysis system 100 will be described with reference to FIG. 15.

In the first illustrative embodiment, the sample solution used for the measurement of the diode array detector 62 of the liquid chromatography device 60 is irradiated with light of a smaller amount, compared with the Fluorescence Spectrophotometer 1, so the photodegraded or photoreactive component may be introduced to the mass spectrometer 70. Therefore, in the third illustrative embodiment, the flow path from the separation column 61 is branched into two flow paths, and by switching the flow path, one is introduced to the diode array detector 62 and the other is introduced to the mass spectrometer 70, so that it becomes possible to obtain mass information of the components of the sample not irradiated with light.

Figure 16:
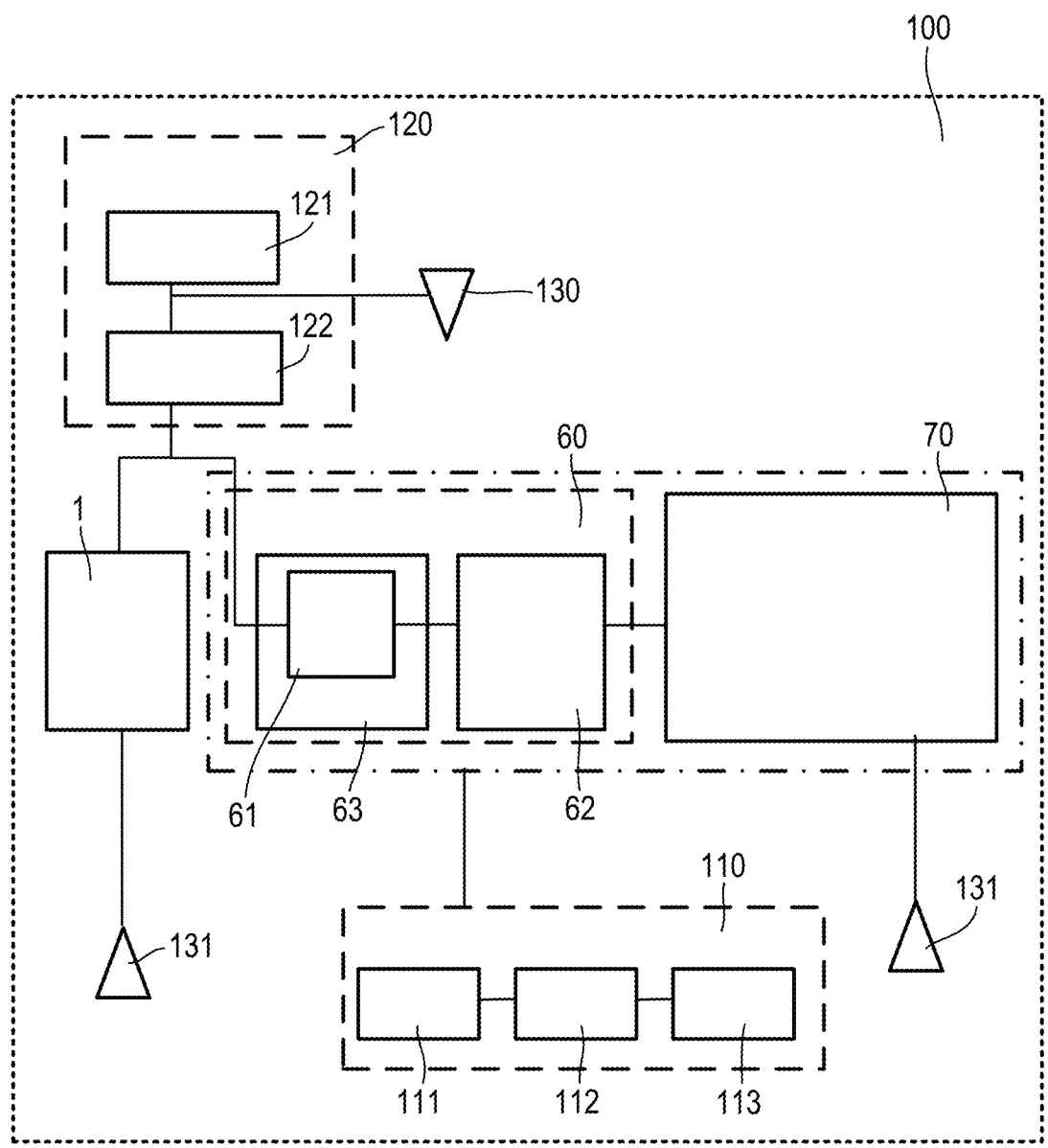
FIG. 16 is a block diagram showing an example of a fourth embodiment of the sample analysis system according to the disclosure.

FIG. 16 is a block diagram showing a fourth illustrative embodiment of the sample analysis system 100. The fourth illustrative embodiment of the sample analysis system 100 will be described with reference to FIG. 16.

In the fourth illustrative embodiment, the Fluorescence Spectrophotometer 1 is controlled by the central processing portion 32, and the liquid chromatography device 60 and the mass spectrometer 70 are controlled by the controller 111. It is configured such that the sample solution used in the Fluorescence Spectrophotometer 1 is led to the waste liquid portion 131 and discarded and a sample in a new state is introduced to the flow path after the separation column 61. The sample measured with the Fluorescence Spectrophotometer 1 is taken out once, artificially transferred to the liquid chromatography device 60, and measured with the liquid chromatography device 60. Various data items are linked with each other, and may be controlled by the control device 110 as a whole.

It is to be noted that the disclosure is not limited to the above-described illustrative embodiment, but can be appropriately modified, improved, and the like. In addition, the material, shape, size, numerical value, form, number, placement place, and the like of each constituent element in the illustrative embodiment described above are arbitrary as far as the disclosure can be achieved, and are not limited. The mass spectrometer is a quadrupole type, an ion, and wrap type, a sector type, or the like, and there is no limitation on its type.

The sample analysis system, the display method, and the sample analysis method according to the disclosure are applicable to fields in which unknown elements are desired to be specified.

What is claimed is:

1. A sample analysis system comprising:
   a Fluorescence Spectrophotometer configured to measure fluorescence emitted by irradiating a sample to be measured with excitation light and to obtain an excitation spectrum indicating a fluorescence intensity with respect to an excitation wavelength and a fluorescence spectrum indicating a fluorescence intensity with respect to a fluorescence wavelength of fluorescence emitted by irradiating the sample with excitation light of a specific wavelength;
   a liquid chromatography device configured to separate the sample into substances contained according to an elution time, and to obtain an absorption wavelength of each of the substances;
   a mass spectrometer configured to obtain mass information of each of substances obtained by separation according to the elution time;
   a display displaying a measurement result; and
   a controller configured to control the Fluorescence Spectrophotometer, the liquid chromatography device, the mass spectrometer, and the display and to, based on a peak of a fluorescence intensity with respect to a specific excitation wavelength and a peak of an absorbance with respect to a specific absorption wavelength, the peak of the absorbance corresponding to the peak of the fluorescence intensity, display on the display mass information corresponding to the elution time at which at least the peak of the absorbance is obtained, the fluorescence intensity being obtained by the Fluorescence Spectrophotometer, the absorbance being obtained by the liquid chromatography device, the mass information being obtained by the mass spectrometer.

2. The sample analysis system according to claim 1, wherein the Fluorescence Spectrophotometer is configured to obtain a three-dimensional fluorescence spectrum including an excitation wavelength, a fluorescence wavelength, and a fluorescence intensity.

3. The sample analysis system according to claim 1, wherein the liquid chromatography device is configured to obtain a three-dimensional absorption spectrum including the elution time, the absorption wavelength, and an absorbance.

4. The sample analysis system according to claim 1, wherein the liquid chromatography device comprises:

a separation column configured to separate the sample into the substances contained according to the elution time; and a diode array detector configured to measure the absorption wavelength of each of the substances separated by the separation column.

5. The sample analysis system according to claim 4, wherein the substances separated by the separation column are introduced into both the diode array detector and the mass spectrometer.

6. The sample analysis system according to claim 1, wherein the mass spectrometer is configured to obtain a three-dimensional mass spectrum including the elution time, the mass information, and an ion intensity.

7. The sample analysis system according to claim 6, wherein the mass information is a mass-charge ratio.

8. The sample analysis system according to claim 1, wherein the mass spectrometer comprises a single or a plurality of mass detectors.

9. The sample analysis system according to claim 1, further comprising:

a sample introducer configured to introduce the sample into the sample analysis system, wherein the sample introducer is configured to introduce the sample into the Fluorescence Spectrophotometer, and wherein the Fluorescence Spectrophotometer is configured to introduce the sample into the liquid chromatography device, after obtaining an excitation spectrum.

10. The sample analysis system according to claim 1, further comprising:

a sample introducer configured to introduce the sample into the sample analysis system, wherein the sample introducer is configured to introduce the sample into both the Fluorescence Spectrophotometer and the liquid chromatography device.

11. The sample analysis system according to claim 1, wherein the controller is configured to:

detect the peak of the fluorescence intensity with respect to the specific excitation wavelength, the fluorescence intensity being obtained by the Fluorescence Spectrophotometer;

specify the peak of the absorbance with respect to the specific absorption wavelength corresponding to the peak of the fluorescence intensity, the absorbance being obtained by the liquid chromatography device; and specify the mass information corresponding to the elution time at which the peak of the absorbance is obtained, the mass information being obtained by the mass spectrometer.

12. The sample analysis system according to claim 1, wherein the Fluorescence Spectrophotometer is configured to obtain a three-dimensional fluorescence spectrum including an excitation wavelength, a fluorescence wavelength, and a fluorescence intensity, wherein the liquid chromatography device is configured to obtain a three-dimensional absorption spectrum including the elution time, the absorption wavelength, and an absorbance, wherein the mass spectrometer is configured to obtain a three-dimensional mass spectrum including the elution time, the mass information, and an ion intensity, wherein the controller is configured to:

set an axis of the excitation wavelength of the three-dimensional fluorescence spectrum and an axis of the absorption wavelength of the three-dimensional absorption spectrum on the same scale; and set an axis of the elution time of the three-dimensional absorption spectrum and an axis of the elution time of the three-dimensional mass spectrum on the same scale, and wherein the controller is configured to control the display to display the three-dimensional fluorescence spectrum, the three-dimensional absorption spectrum, and the three-dimensional mass spectrum side by side.

13. A display method using a sample analysis system, the sample analysis system comprising a Fluorescence Spectrophotometer, a liquid chromatography device, a mass spectrometer, and a display displaying a measurement result, the display method comprising:

setting an axis of an excitation wavelength of a three-dimensional fluorescence spectrum obtained by the Fluorescence Spectrophotometer and an axis of an absorption wavelength of a three-dimensional absorption spectrum obtained by the liquid chromatography device on the same scale;

setting an axis of an elution time of the three-dimensional absorption spectrum and an axis of an elution time of a three-dimensional mass spectrum on the same scale, the three-dimensional mass spectrum being obtained by the mass spectrometer; and controlling the display to display the three-dimensional fluorescence spectrum, the three-dimensional absorption spectrum, and the three-dimensional mass spectrum side by side.

14. A sample analysis method implemented using a sample analysis system, the sample analysis system comprising a Fluorescence Spectrophotometer, a liquid chromatography device, and a mass spectrometer, the sample analysis method comprising:

detecting a peak of a fluorescence intensity for a specific excitation wavelength, the fluorescence intensity being obtained by the Fluorescence Spectrophotometer;

specifying a peak of an absorbance with respect to a specific absorption wavelength corresponding to the peak of the fluorescence intensity, the absorbance being obtained by the liquid chromatography device; and specifying mass information corresponding to an elution time at which the peak of the absorbance is obtained, the mass information being obtained by the mass spectrometer.

* * * * *